United States Patent [19]

Muldashev et al.

[11] 4,383,338
[45] May 17, 1983

[54] HOMOTRANSPLANT FOR CONJUNCTIVIPLASTY

[76] Inventors: Ernst R. Muldashev, ulitsa Rossiiskaya 17/2, kv. 94; Rafik T. Nigmatullin, ulitsa Vostretsova, 14, kv. 19; Venera U. Galimova, ulitsa Ulyanovykh, 20, kv. 74; Klara A. Zakhvatkina, ulitsa 8 Marta, 63, kv. 63; Sagit A. Muslimov, ulitsa Aralskaya, 21, kv. 1, all of Ufa, U.S.S.R.

[21] Appl. No.: 246,038

[22] Filed: Mar. 20, 1981

[51] Int. Cl.³ .......................... A61F 1/16; A61F 1/24
[52] U.S. Cl. ................................................. 3/13; 3/1; 8/94.11; 128/1 R
[58] Field of Search ............. 3/1, 13; 128/1 R, 334 R, 128/305; 8/94.11

[56] References Cited

U.S. PATENT DOCUMENTS 3,988,782  11/1976  Dardik et al. .................... 3/13 X

OTHER PUBLICATIONS

V. P. Filatov, Pterygoid Operations, 1960, Manual for Eye Diseases, vol. 5, pp. 30–34.
B. I. Ismailoff, Some Facts of Pterygium Among Kara--Kalpak Inhabitants, 1978, Oftalmologichesky Zhurnal, No. 6, pp. 471–472.
S. A. Barkhash, Placenta as a Plastic Material in Ophthalmosurgery, 1940, Vestnik Oftalmologii, No. 6, pp. 758–761.
B. I. Tikhvinsky, Use of Egg Membrane for Eyeball Plastic Surgery, 1938, Vestnik Oftalmologii, vol. 13, pp. 397–401.
N. A. Ushakov & P. T. Chesnokov, Use of a Gullet Homomucous Layer in Ophthalmosurgery, 1972, Leningrad, vol. 191, pp. 73–76.
N. A. Puchkovskaya et al., Pathogenesis and Treatment of Eye Burns, 1973, Moscow, pp. 129–130.
Data on the Prevalance of the Blind in the World, 1979, Chronicle of World Health Organization, No. 11, pp. 562–570.
Y. V. Legese, Homotransplanatation of Mucous Membrane, 1970, Abstract of Thesis for a Doctorate, Odessa, pp. 21–25.
O. D. Morozova, Corneal Conjunctival Plastic Surgery, 1971, Vestnik Oftalmologii, No. 2, pp. 24–26.

*Primary Examiner*—Ronald L. Frinks
*Attorney, Agent, or Firm*—Murray Schaffer

[57] ABSTRACT

The homotransplant for conjunctiviplasty is essentially a retroperitoneal fascia. The use of the proposed homotransplant facilitates procurement of the material for homoplasty, said material can be taken in a large amount at a time and is readily transportable, the operation is facilitated and rendered less traumatic, the operating time is cut down, the cosmetic and clinical effect of the operation is improved, and the postoperative period is reduced.

2 Claims, No Drawings

HOMOTRANSPLANT FOR CONJUNCTIVIPLASTY

FIELD OF THE INVENTION

The present invention relates to the art of medicine, more specifically to ophthalmology, and has particular reference to homotransplants for conjunctiviplasty.

The invention is applicable for plastic surgery on the eyeball conjunctiva to eliminate morbid effect caused by trachoma and burns, as well as in the cases of fresh burns, the Stevens-Johnson syndrome, tumors of various ethiology, pterygium, and every kind of injuries.

BACKGROUND OF THE INVENTION

The plastic surgery of the conjunctiva is one of the urgent problems the present-day ophthalmological practice is faced with. It is not infrequently that the conjunctiva gets affected by burns, the incidence of which amounts to 20.3 percent of the total cases of the eye injuries (cf. N. A. Puchkovskaya et al., "Pathogenesis and treatment of burns of the eye and of their sequels", Moscow, 1973, pp. 129 to 130/in Russian/). Furthermore the conjunctiva is the location of various tumours (cf. Aftab M., Pergival S.P.B. "Basal Cell Carcinoma of the Conjunctiva", Brit. J. Ophthal., 1973, 57, 11, pp. 836–837), may be affected by pemphigus, lupus, Dühring's disease, and Stevens-Johnson disease (cf. N. A. Puchkovskaya, "Keratoplasty in complicated cases of leukoma", Kiev, 1960, pp. 21, 127). There occurs widely such a disease as pterygium, its incidence in the steppe areas of the Soviet Union amounting to 21 percent of the polulation (cf. B. I. Ismailov, "Some data on the incidence of pterygium in the inhabitants of the Kara-Kalpak ASSR regions", Oftalmologichesky zhurnal (Ophthalmological Journal), 1978, No. 6, pp. 471-472). A vast multitude of trachoma patients occur in the world up till now (cf. Chronicle of World Health Organization, 1979, No. 11).

A majority of patients suffering from the abovesaid diseases want plastic surgery on the conjunctiva. At present most widely applicable for the purposes of conjunctiviplasty are autografts of the mucosa of the lip (cf. N. A. Puchkovskaya et al., "Pathogenesis and treatment of burns of the eye and of their sequels", Moscow, 1973, pp. 129 to 130). However, taking a graft of the mucosa of the lip is a very traumatic manipulation sometimes fraught with eversion of the lip, whereas cosmetic effect of the operation proves to be unsatisfactory as the transplanted mucosa of the lip stands out by its bright-red colour (cf. O. D. Morozova, "Kerato- and conjunctiviplasty in surgical treatment of symblepharon and recurrent pterygium". Vestnik oftalmologii (Ophthalmological herald), 1971, No. 2, pp. 24 to 26).

Known heretofore in the art is the use of homografts of the eyeball conjunctiva (cf. Byerly Holt L. Eye Tissue Transplantation in Children. Eye, Ear, Nose, Throat Monthly, 1970, 49, L., pp. 172 to 174; Järplid B., Schantz B. Rejection of Skin and Conjunctival Allograft in the Dog after Prolonged Graft Survival. Acta Chir. Scand., 1973, 139, 6, pp. 517 to 521); however, good results of such operations are far from being obtained at all times. In addition, some difficulties are encountered in procurement of eyes from cadavers (cf. Paton R. T., Keratoplasty. New-York, 1955). The same disadvantages are inherent in conjunctiviplasty using the cornea procured from cadavers (cf. V. P. Filatov, "Surgery for pterygium". In his textbook "Manual for Eye Diseases", 1960, v.5, pp. 30–34/in Russian/). There were suggested also homografts of the mucosa of the lip (cf. G. V. Legeza, "Homotransplantation of the mucosa in surgical treatment of sequels of eye burns", an abstract of the thesis for a doctorate, Odessa, 1970), and those of the esophageal mucosa (cf. N. A. Ushakov, P. T. Chesnokov, "Problems of reconstructive ophthalmoplasty", Leningrad, 1972, v.191 pp. 73–74/Russian/) proved to yield a good effect only for reparation of small defects of the conjunctiva.

An experimental use of a homovenous wall is known to have been made for conjunctiviplasty (cf. Français I., Udal-On M. La paroi veineuse pour korrogreffe de la conjonctive. Ann. Oculist., Paris, 1972, 205, 4, pp. 447 to 457).

Some reports are now available about the application of vaginal mucosa as homografts for conjunctiviplasty (cf. A. A. Kolen, "On use of vaginal mucosa for plastic reconstruction of the conjunctival sac". A collection of papers by Prof. N. I. Gorizontov, Novosibirsk, 1935), of placenta (cf. S. A. Barkhash, "Placenta as a material for plastic surgery". Vestnik oftalmologii, 1040, No. 6, p. 758), or of egg's membrane (cf. B. I. Tikhvinsky, "On use of egg's membrane for plastic surgery on the eyeball". Vestnik oftalmologii, 1938, v.13, p.397).

However, every kind of homografts suggested heretofore fails to satisfy ophthalmic surgeons, as some of them are clinically low efficient, while some other are hardly procurably in great amounts (such as conjunctiva, mucosa of the vagina or lip) or are difficult to fix with sutures (placenta).

SUMMARY OF THE INVENTION

It is therefore a primary and essential object of the present invention to provide a readily available material for plastic reconstruction of the conjunctiva, procure said material in greater amounts and attain a better clinical and cosmetic effect of said operation.

The aforesaid and other objects are accomplished due to the provision of a homotransplant for conjunctiviplasty which, according to the present invention, is essentially a retroperitoneal fascia.

DETAILED DISCLOSURE OF THE INVENTION

The retroperitoneal fasciae, such as *fascia transversa*, *fascia retroperitonealis* are procured from cadavers when autopsy is carried out under nonsterile conditions, by separating them from the adjacent anatomical structures. Procurement of these fasciae is contrary neither to national and religious traditions nor to routine living situations as being carried out during autopsy and not deteriorating the appearance of the decedent. The thusseparated fasciae are cleansed and put in 70-percent ethanol to be stored there until getting sterile. Further the material is packed, when stretched out, in cellophane bags or glass weighing bottles, 70-percent ethanol being used as a preservative. The material is to be stored at a temperature of from zero to 30° C. The storage term of the thus-procured transplants may range within seven days to four years and even more. The preserved material is readily transportable in a packed state. There may be procured from a single cadaver an amount of the material large enough to carry out over 80 operations for reconstructive conjunctiviplasty. In addition, retroperitoneal fasciae have an optimum thickness suitable for plastic reconstruction of the conjunctiva.

Experimental studies into the homoplasty of the conjunctiva with the use of a retroperitoneal fascia have been performed on 60 test rabbits. Two runs of experiments have been carried out, viz, in the first run of experiments the conjunctival defect has been repaired by the homograft of a retroperitoneal fascia, while in the second run of experiments, by the conjunctival homograft. Then the both kinds of transplants have been studied biomicroscopically and morphologically on the 3rd, 7th, 14th, 21st, 30th, 60th, 90th, 120th and 180th days after the operation. The studies performed have demonstrated the homografts of a retroperitoneal fascia to cause but a weaker tissue reaction compared to the conjunctival homografts, while the surface of the former homografts gets covered conjunctical epithelium within an earlier period (on the 3rd or 7th day). Further on the fascial homograft is replaced by a tissue similar to that of the conjunctiva, whereas the conjunctival homografts are as a rule liable to more or less pronounced cicatricial deformation.

The operative techniques involving the use of the proposed homograft are as follows.

The defect of the eyeball conjunctive resulting from, say, operative elimination of symblepharon, is stripped of cicatricial tissue, whereupon the homograft of a retroperitoneal fascia is taken out of the preserving solution and a reparative patch is cut out of it to suit the shape of the conjunctival defect. This done, the patch is put onto the defected spot of, say, the eyeball conjunctiva, after which the homograft is fixed by sutures at its margins to the episclera so that it should be arranged evenly over the episcleral surface and be in somewhat tensioned state. Within the postoperative period disinfecting drops are instilled into the conjunctival sac, no immunodepressive therapy being resorted to. The patients operated upon are dismissed on the 5th–15th day after the operation of the graft surface have occurred.

Homografts of a retroperitoneal fascia may be applied for reparation of the defects of eyeball conjunctiva having any size, up to total defects, as well as in the defects of conjunctiva of eyelids. Conjunctival homoplasty using a retroperitoneal fascia may be combined with layer-layer keratoplasty.

A total of 308 patients (326 eyes) have been operated upon for the sequels of burns, trachoma, injuries, primary and recurrent pterygium, benign and malignant tumors, and fresh burns with the use of the proposed homograft. Late results of the operations performed have been observed within a period of six years. In every case the homografts of a retroperitoneal fascia are found to have been reimplanted well and to repair stably the conjunctival defect. Good cosmetic effect has been observed in 96.4 percent of cases, while a stable clinical effect of the operation (i.e., no relapses, adequate depth of the conjunctival fornices) has been found in 90.8 percent of cases.

The proposed transplant is advantageous over the heretofore known materials for surgical ophthalmoplasty in the following.

Facilitated procurement of the material as the superficial coverings of a cadaver remain intact and the material is taken up during conventional autopsy. Possibility of procuring a great amount of material at a time and its simple preservation for prolonged periods, which are good prerequisites for establishing a large stock of transplants. Procurement of the proposed ophthalmoplastic material needs no preparation of highly skilled specialists and costly preservatives and is therefore economically beneficial.

Unlike autoplastic operations using the known autografts (from the mucosa of patient's lip) homoplasty with a retroperitoneal fascia renders the operation less traumatic and cuts down the operating time. Furthermore the cosmetic effect of the operation is much improved, while being not inferior to autoplastic method as to clinical results. A comparative analysis carried out on similar clinical data within a period of 5 years has demonstrated that a good cosmetic effect has been attained in 59 cases out of 62 (95.2 percent) with the use of homografts of a retroperitoneal fascia, whereas such an effect with the use of autografts of the mucosa of the lip has been obtained only in 8 cases out of 48 (16.6 percent), a good clinical effect having been observed in 90.3 and 87.4 percent of the cases, respectively.

In contrast to the heretofore known homografts made of the mucosa of the lip, the esophagus, the vagina, the conjunctiva, the use of a retroperitoneal fascia for making a homograft adds much to the clinical effect of the operation and provides for a possibility of performing plastic reconstruction of large defects of the conjunctiva. Costly immunodepressive agents may be dispensed with within the postoperative period, while the latter period is reduced two times. Comparative experimental studies have shown that in conjunctival homoplasty with a retroperitoneal fascia cicatricial deformations (occuring on the 120th day) have been observed in 7.2 percent of cases, whereas those in homoplasty with conjunctival tissue have been found in 63 percent of cases. A positive and favourable factor in this respect is the absence of its own epithelial lining in the homografts made of a retroperitoneal fascia, whereas a majority of the heretofore known homografts have such a lining; the epithelium of these homografts is inevitably rejected, thus increasing the immune reaction. Homotransplanting with the use of a retroperitoneal fascia establishes optimum conditions for epithelization of said fascia, whereby the own epithelial lining is restored at the place of the homograft as early as within 3 to 5 days after the operation. As immune reaction is negligible the homograft gets replaced without any marked cicatricial changes.

Finally the operational techniques are made easier as the retroperitoneal fascia is firmly fixed with sutures, which is accounted for by specific features of its fibrostructure.

What is claimed is:

1. A homotransplant for conjunctiviplasty, comprising a non-viable preserved retroperitoneal fascia.

2. The homotransplant according to claim 1 wherein said retroperitoneal fascia has been preserved in ethanol for at least 7 days.

* * * * *